(12) United States Patent
Hirota et al.

(10) Patent No.: US 7,765,636 B2
(45) Date of Patent: Aug. 3, 2010

(54) VACUUM CLEANER AND DUST BAG FOR VACUUM CLEANER

(75) Inventors: Masanobu Hirota, Shiga (JP); Hiroyuki Kayama, Osaka (JP); Makoto Murakami, Osaka (JP); Koichi Nakano, Osaka (JP); Hidenori Kitamura, Shiga (JP); Tomomi Mitani, Shiga (JP); Takaaki Ogawa, Shiga (JP); Ryouhei Yoshida, Shiga (JP)

(73) Assignee: Panasonic Corporation, Osaka (JP)

( * ) Notice: Subject to any disclaimer, the term of this patent is extended or adjusted under 35 U.S.C. 154(b) by 977 days.

(21) Appl. No.: 11/362,753

(22) Filed: Feb. 28, 2006

(65) Prior Publication Data

US 2006/0191416 A1    Aug. 31, 2006

(30) Foreign Application Priority Data

| Feb. 28, 2005 | (JP) | ............................. 2005-052802 |
| Mar. 10, 2005 | (JP) | ............................. 2005-066979 |
| Mar. 31, 2005 | (JP) | ............................. 2005-102152 |
| Mar. 31, 2005 | (JP) | ............................. 2005-102154 |
| Aug. 1, 2005  | (JP) | ............................. 2005-222358 |

(51) Int. Cl.
A47L 7/04 (2006.01)
A47L 9/12 (2006.01)

(52) U.S. Cl. .............................. 15/339; 15/246.3; 422/5

(58) Field of Classification Search ................ 15/246.3, 15/339; 422/5; *A47I 7/04, 9/00, 9/12*
See application file for complete search history.

(56) References Cited

U.S. PATENT DOCUMENTS

| 1,881,086 A | * | 10/1932 | Marshall ....................... 96/226 |
| 3,274,758 A | * | 9/1966 | Parman ........................ 96/222 |
| 5,040,264 A | | 8/1991 | Bryant |
| 5,964,404 A | * | 10/1999 | Randolph ..................... 239/56 |

FOREIGN PATENT DOCUMENTS

| CN | 1365262 | | 8/2002 |
| DE | 3740517 | | 6/1989 |
| DE | 10030958 | | 2/2001 |
| DE | 10030958 A1 | * | 2/2001 |
| DE | 1350457 | | 10/2003 |
| DE | 10352921 | | 6/2005 |
| EP | 1495709 | | 1/2005 |
| JP | 2-237526 | | 9/1990 |

(Continued)

OTHER PUBLICATIONS

Shenping et al., Shao; "Hydrophobic Silicone Zeolite Molecular Sieve", China Academic Journal Electronic Publishing House, p. 40-42.

(Continued)

*Primary Examiner*—David A Redding
(74) *Attorney, Agent, or Firm*—Bacon & Thomas, PLLC

(57) ABSTRACT

A vacuum cleaner includes a dust chamber, a dust bag provided in the dust chamber, and an electric blower for generating suction air flow for drawing and collecting dust and dirt in the dust bag. A deodorant is supplied into the dust bag by the suction air flow and directly attached to the dust and dirt. The deodorant has a granule or powder shape.

28 Claims, 11 Drawing Sheets

FOREIGN PATENT DOCUMENTS

| | | |
|---|---|---|
| JP | 3-231019 | 10/1991 |
| JP | 4-251253 | 9/1992 |
| JP | 5-84191 | 4/1993 |
| JP | 6-70871 | 3/1994 |
| JP | 9-122049 | 5/1997 |
| JP | 2810090 | 7/1998 |
| JP | 3289226 | 3/2002 |

OTHER PUBLICATIONS

Huang et al., He; "Development of deodorizing finish", China Academic Journal Electronic Publishing House, p. 39-41.

* cited by examiner

RELATIONSHIP BETWEEN GRANULE DIAMETER
AND ODOR STRENGTH OF DUST AND DIRT

RELATIONSHIP BETWEEN GRANULE DIAMETER
AND INJECTION AMOUNT

VACUUM CLEANER AND DUST BAG FOR VACUUM CLEANER

FIELD OF THE INVENTION

The present invention relates to a vacuum cleaner and a dust bag for a vacuum cleaner; more particularly, to deodorization of dust collected in a dust bag.

BACKGROUND OF THE INVENTION

As for a conventional method for deodorizing dust and dirt collected in a dust bag for a vacuum cleaner, a dust bag or dust filter is impregnated with a deodorant so that odor of the dust and dirt is removed by the deodorant (see, for example, Japanese Patent Laid-open Application No. H06-70871: Reference 1).

It has also been proposed to install a deodorizing aromatic in a space inside a dust chamber of a vacuum cleaner, which contains a dust bag for the vacuum cleaner (see, for example, Japanese Patent No. 2810090: Reference 2).

However, the conventional deodorizing method disclosed in Reference 1 has a problem in that, since only the filtering material of the dust bag or dust filter is impregnated with the deodorant, the contact area of the filtering material with dust and dirt is small and the contact time thereof is instantaneous, which means that the deodorizing effect is insufficient. Therefore, when a vacuum cleaner having the conventional dust bag or dust filter mounted thereon is operated, the air flow discharged from the vacuum cleaner smells of an unpleasant odor, depending on the type or staying period of dust and dirt.

Further, in the conventional configuration disclosed in Reference 2, the odor of air discharged from the vacuum cleaner is proposed to be alleviated by spreading a deodorizing component over the dust chamber and deodorizing the dust and dirt inside the dust bag by means of installing the deodorizing aromatic in the space inside the dust chamber. The deodorizing aromatic, which adds a separate fragrance to the odor of dust and dirt, has a limitation in that, although it may alleviate the odor of the discharged air to some degree, it cannot remove the odor fundamentally. Further, depending on the type of drawn dust and dirt, the fragrance from the aromatic may be discharged from the vacuum cleaner as another unpleasant smell.

In the conventional configuration, a dust bag-type cleaner, which is adapted to draw in dust and dirt in a large quantity and holds them for a long period of time, has a problem in that, since the air flow drawn therein passes through almost all dust and dirt, the amount of generated odor increases in proportion to the amount of the dust and dirt drawn therein. As the amount of collected dust and dirt reaches a threshold value of the dust bag, the amount of the generated odor increases sharply and it is almost impossible to obtain a desired deodorizing effect with a deodorizing aromatic.

SUMMARY OF THE INVENTION

It is, therefore, an object of the present invention to provide a vacuum cleaner and a dust bag for a vacuum cleaner capable of substantially reducing the odor resulting from dust and dirt in the air discharged from the vacuum cleaner during an operation of the vacuum cleaner, regardless of the amount or staying period of the dust and dirt held inside the dust bag, for convenient and pleasant use.

In accordance with a preferred embodiment of the present invention, there is provided a vacuum cleaner including: a dust chamber; a dust bag provided in the dust chamber; and an electric blower for generating suction air flow for drawing and collecting dust and dirt in the dust bag, wherein a deodorant is supplied into the dust bag by the suction air flow and directly attached to the dust and dirt, the deodorant having a granule or powder shape. The deodorant of the granule or powder shape uniformly diffuses across the dust and dirt and is attached to the surface thereof, so that the odor resulting from the dust and dirt is directly removed. As a result, any odor resulting from the dust and dirt is not included in the suction air flow. In addition, the deodorant continues to be present until the dust bag is thrown away or the envelope-shaped body is emptied, so that discharged air is free from odor for a long period of time.

In accordance with another preferred embodiment of the present invention, there is provided the vacuum cleaner, wherein the dust bag includes a core mounted inside the vacuum cleaner and provided with an opening for drawing in the dust and dirt; an envelop-shaped body for collecting the dust and dirt drawn via the opening of the core; and a storage case containing therein the deodorant and communicating with the opening of the core. As a result, the contact area of the deodorant with the dust and dirt is substantially large. Further, the deodorant continues to be present until the dust bag is thrown away or the envelope-shaped body is emptied. Therefore, an excellent deodorizing effect persists for a long period of time, thereby enabling a convenient and pleasant cleaning.

In accordance with still another preferred embodiment of the present invention, there is provided the vacuum cleaner, wherein the dust bag includes a storage case containing therein the deodorant; an air-permeable envelope disposed so as to cover an opening end of the storage case; a core mounted inside the vacuum cleaner and provided with an opening for drawing in the dust and dirt, a part of the air-permeable envelope being protruded into the opening of the core; and an envelop-shaped body for collecting the drawn dust and dirt. The dust bag is operated as follows: an air flow, which is generated when the vacuum cleaner is operated, reaches the air-permeable portion of the storage case and extrudes the deodorant of the granule or powder shape, which is gathered in the air-permeable portion, into the envelope-shaped body. The deodorant is uniformly attached to the surface or inside of the collected dust and dirt to deodorize the dust and dirt in their vicinity, where the deodorizing effect is strongest. Further, the deodorant can maintain the deodorizing performance for a long period of time regardless of the amount of the dust and dirt held inside the envelope-shaped body.

In accordance with still another preferred embodiment of the present invention, there is provided the vacuum cleaner, wherein the dust bag has an envelop-shaped body for collecting the dust and dirt, and the deodorant is provided in the envelop-shaped body in advance and attached to the dust and dirt in the envelope-shaped body by at least one of the suction air flow and vibration of the dust bag. The dust bag is advantageous in that, since the deodorant of the granule or powder shape is attached to dust and dirt inside the envelope-shaped body by at least one of the suction air flow or vibration, the dust and dirt remaining in the envelope-shaped body are continuously deodorized so that the odor included in discharged air is reduced substantially.

In accordance with still another preferred embodiment of the present invention, there is provided the vacuum cleaner, wherein the deodorant is supplied into the dust bag at a weight ratio ranging from about 0.5 wt % to about 5 wt % with respect to the dust and dirt in the dust bag. This makes it possible to maintain a desired deodorizing capacity based on the odor level of the dust and dirt.

In accordance with still another preferred embodiment of the present invention, there is provided the vacuum cleaner, wherein the deodorant has a granule diameter equal to or greater than 0.1 µm and equal to or less than 1 mm. If the granule diameter is larger than 1 mm, particles are too large, when the particles are injected into the envelope-shaped body, to make the deodorant fully cover the surface of dust and dirt. Further, the deodorant has a smaller surface area for adsorbing odor components and exhibits a poor deodorizing effect in comparison with the case of particles of a smaller diameter of the same weight.

If the granule diameter is smaller than 0.1 µm, slipping properties among particles are poor. In other words, the fluidity is degraded. This makes it difficult to smoothly inject the deodorant from the storage case. For these reasons, granule diameter of 0.1 µm to 1 mm is optimal to smoothly inject the deodorant into the envelope-shaped body and realize a vacuum cleaner having an excellent deodorizing effect.

In accordance with still another preferred embodiment of the present invention, there is provided the vacuum cleaner, wherein the deodorant includes at least one of hydrophobic zeolite, active carbon and transition metal oxide. The deodorant can efficiently remove complex odors resulting from dust and dirt collected in the vacuum cleaner.

In accordance with still another preferred embodiment of the present invention, there is provided the vacuum cleaner, wherein the deodorant has a functional material added thereto. In this manner, the deodorant may incorporate additional functions besides basic functions.

In accordance with still another preferred embodiment of the present invention, there is provided the vacuum cleaner, wherein the functional material is a hygroscopic material. This is for the purpose of drying dust and dirt inside the vacuum cleaner and preventing germs from multiplying. In addition, as the deodorant absorbs moisture, the powdery deodorant has a sufficient fluidity to be injected into the envelope-shaped body easily.

In accordance with still another preferred embodiment of the present invention, there is provided the vacuum cleaner, wherein the functional material serves to improve fluidity of the deodorant. Improved fluidity of the deodorant makes it possible to inject the deodorant into the envelope-shaped more efficiently.

In accordance with still another preferred embodiment of the present invention, there is provided the vacuum cleaner, wherein the functional material is an antibacterial material. The antibacterial material prevents germs from multiplying in the envelope-shape body.

In accordance with still another preferred embodiment of the present invention, there is provided the vacuum cleaner, wherein the functional material is an aromatic material. As an aroma is added to the air discharged from the vacuum cleaner, which has been deodorized, a pleasant space is provided.

In accordance with still another preferred embodiment of the present invention, there is provided a dust bag for a vacuum cleaner including: a core mounted in the vacuum cleaner and provided with an opening for drawing in dust and dirt; an envelope-shaped body for collecting the dust and dirt drawn via the opening of the core; and a storage case communicating with the opening of the core and containing therein a deodorant of a granule or powder shape. The deodorant of the granule or powder shape, which is discharged from the storage case by suction air flow for introducing dust and dirt, is mixed with the introduced dust and dirt and is accumulated inside the envelope-shaped body. As a result, the contact area of the deodorant with the dust and dirt is substantially large. In addition, the deodorant continues to be present until the dust bag is thrown away or the envelope-shaped body is emptied. Therefore, an excellent deodorizing effect persists for a long period of time, thereby enabling convenient and pleasant cleaning.

In accordance with still another preferred embodiment of the present invention, there is provided the dust bag for the vacuum cleaner, wherein the storage case is disposed downstream from the core. As a result, the dust bag is applicable to a conventional vacuum cleaner, which is adapted to use a dust bag having no storage case. This improves the compatibility and simplifies the manufacturing or management of the dust bag.

In accordance with still another preferred embodiment of the present invention, there is provided the dust bag for the vacuum cleaner, wherein one or more discharge ports for discharging the deodorant are provided on a surface of the storage case, the surface being substantially parallel to an air flow drawn via the opening of the core. As a result, the deodorant of the granule or powder shape is discharged from the storage case via the discharge port by the action of the suction air flow in a continuous and efficient manner. This guarantees an excellent deodorizing effect.

In accordance with still another preferred embodiment of the present invention, there is provided the dust bag for the vacuum cleaner, wherein the storage case is provided with a detachable cover member which serves to cover the discharge ports when the storage case is not loaded in the vacuum cleaner. As the discharge port is covered with the cover member, the deodorant is not leaked from the storage case when the dust bag for a vacuum cleaner is transported. This guarantees unhindered use of the dust bag for a vacuum cleaner.

In accordance with still another preferred embodiment of the present invention, there is provided a dust bag for a vacuum cleaner including: a storage case containing therein a deodorant of a granule or powder shape; an air-permeable envelope covering an opening end of the storage case; a core mounted in the vacuum cleaner and provided with an opening for drawing in dust and dirt, a part of the air-permeable envelope being protruded into the opening of the core; and an envelop-shaped body for collecting the drawn dust and dirt. The dust bag is operated as follows: an air flow, which is generated when the vacuum cleaner is operated, reaches the air-permeable portion of the storage case and extrudes the deodorant of the granule or powder shape, which is gathered in the air-permeable portion, into the envelope-shaped body. The deodorant is uniformly attached to the surface or inside of the collected dust and dirt to deodorize the dust and dirt in their vicinity, where the deodorizing effect is strongest. Further, the deodorant can maintain the deodorizing action for a long period of time regardless of the amount of the dust and dirt inside the envelope-shaped body.

In accordance with still another preferred embodiment of the present invention, there is provided the dust bag for the vacuum cleaner, wherein the air-permeable envelope has a horizontal cross sectional area gradually decreasing toward the opening of the core. The deodorant easily sinks, due to gravity, into a region of the air-permeable envelope, which protrudes into the opening end of the core, by means of a vibration or an impact generated when the vacuum cleaner is moved, for example. As a result, the deodorant is stably injected into the envelope-shaped body without remaining in the storage case.

In accordance with still another preferred embodiment of the present invention, there is provided the dust bag for the vacuum cleaner, wherein the air-permeable envelope is formed by shaping an air-permeable material into an envelope shape. This makes it easy to manufacture an air-permeable envelope, into which the deodorant can be injected stably.

In accordance with still another preferred embodiment of the present invention, there is provided a dust bag for a vacuum cleaner including: an envelop-shaped body for collecting therein dust and dirt, wherein a deodorant provided in the envelop-shaped body in advance and attached to the dust and dirt in the envelope-shaped body by at least one of a suction air flow and vibration of the dust bag. The dust bag is advantageous in that, since the deodorant of the granule or powder shape is attached to dust and dirt inside the envelope-shaped body by at least one of the suction air flow or vibration, the dust and dirt remaining in the envelope-shaped body are continuously deodorized so that the odor included in discharged air is reduced substantially.

In accordance with still another preferred embodiment of the present invention, there is provided the dust bag for the vacuum cleaner, wherein the envelope-shaped body is formed of multiple layers of envelopes, and the deodorant is detachably fixed to an innermost layer of the envelope via an attachment means.

When the electric blower generates a suction air flow or when introduced dust and dirt collide with the envelope-shaped body and generate an impact, a part of the deodorant collapses accordingly and is mixed with the dust and dirt. The mixed deodorant diffuses into the dust and dirt under the influence of the suction air flow. In addition, the suction air flow passes through the envelope, which has the deodorant attached thereto. This prevents the dust and dirt from generating odor and efficiently removes any already-generated odor.

In accordance with still another preferred embodiment of the present invention, there is provided the dust bag for the vacuum cleaner, wherein the envelope-shaped body is formed of multiple layers of envelopes, and the deodorant is loaded between an outside of an innermost layer of envelope and another layer of envelope.

When the envelope-shaped body is subjected to a suction air flow or vibration, a suitable amount of deodorant is detached from the innermost envelope to be attached to dust and dirt inside the envelope-shaped body. This avoids generation of odor. The air-permeable diameter of the innermost envelope of the plurality of envelopes is larger than the powder diameter of the deodorant, while the air-permeable diameter of other envelopes is smaller than the powder diameter of the deodorant. As a result, the odorant remains in the envelope-shaped body without leaking, even when the electric blower generates a vibration during suction, and avoids generation of any odor.

In accordance with still another preferred embodiment of the present invention, there is provided the dust bag for the vacuum cleaner, an air-permeable envelope is provided inside the envelope-shaped body, and the deodorant is loaded in the air-permeable envelope. This makes it easier to install the deodorant in the envelope-shaped body. When the envelope-shaped body is subjected to a suction air flow or vibration, a suitable amount of deodorant is detached from the air-permeable envelope to be attached to dust and dirt inside the envelope-shaped body. This avoids generation of odor.

In accordance with still another preferred embodiment of the present invention, there is provided the dust bag for the vacuum cleaner, wherein the dust bag is made of one or more flammable materials. The dust bag can be disposed of in an easy and sanitary manner by simply burning it without separating wastes.

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PREFERRED EMBODIMENTS

Hereinafter, embodiments of the vacuum cleaner in accordance with the present invention will be described with reference to the accompanying drawings. It is to be noted that the following description of embodiments does not limit the present invention in any manner.

First Preferred Embodiment

Figure 1:
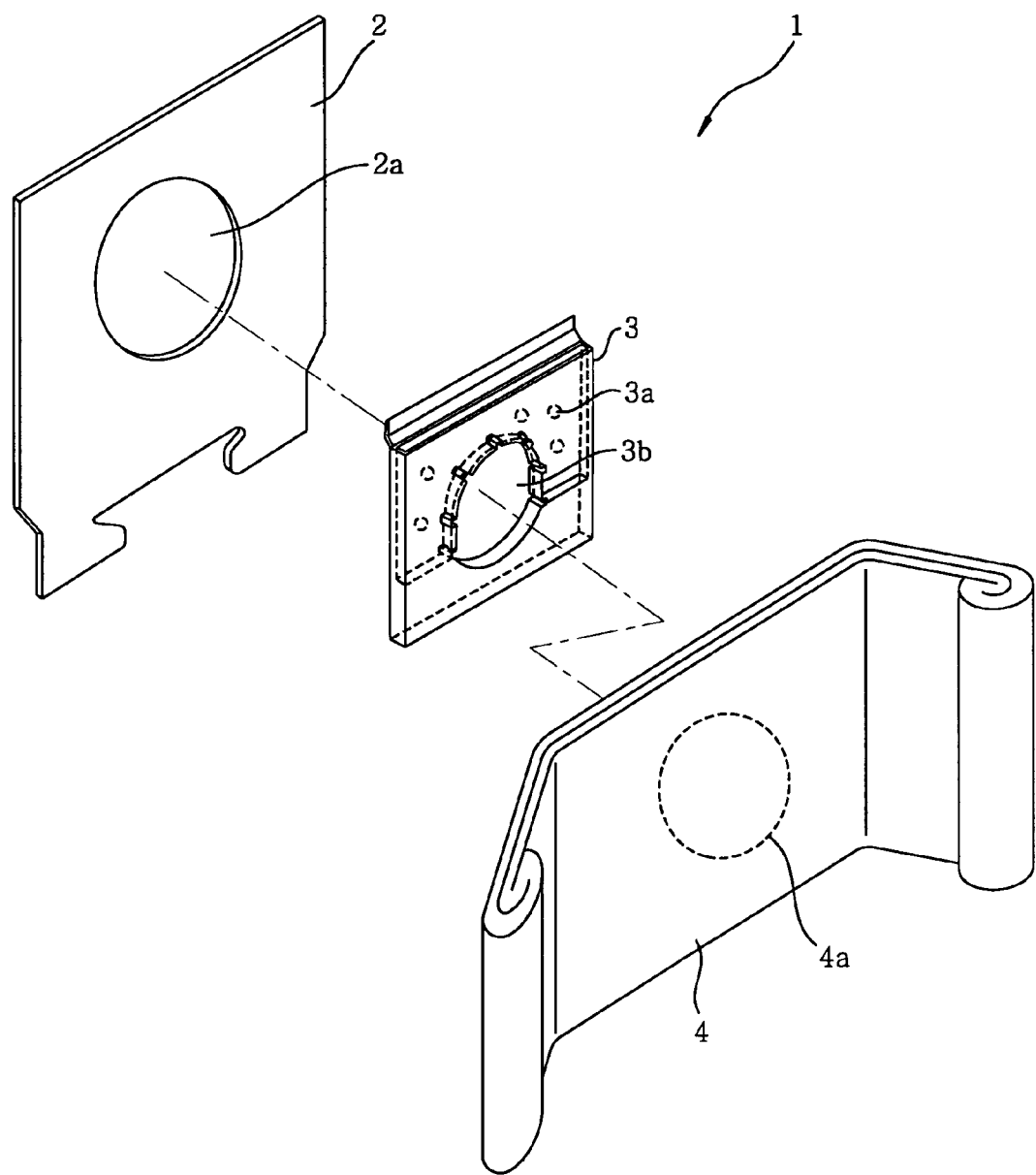
FIG. 1 is an exploded perspective view showing a dust bag for a vacuum cleaner in accordance with a first preferred embodiment of the present invention.
Figure 2:
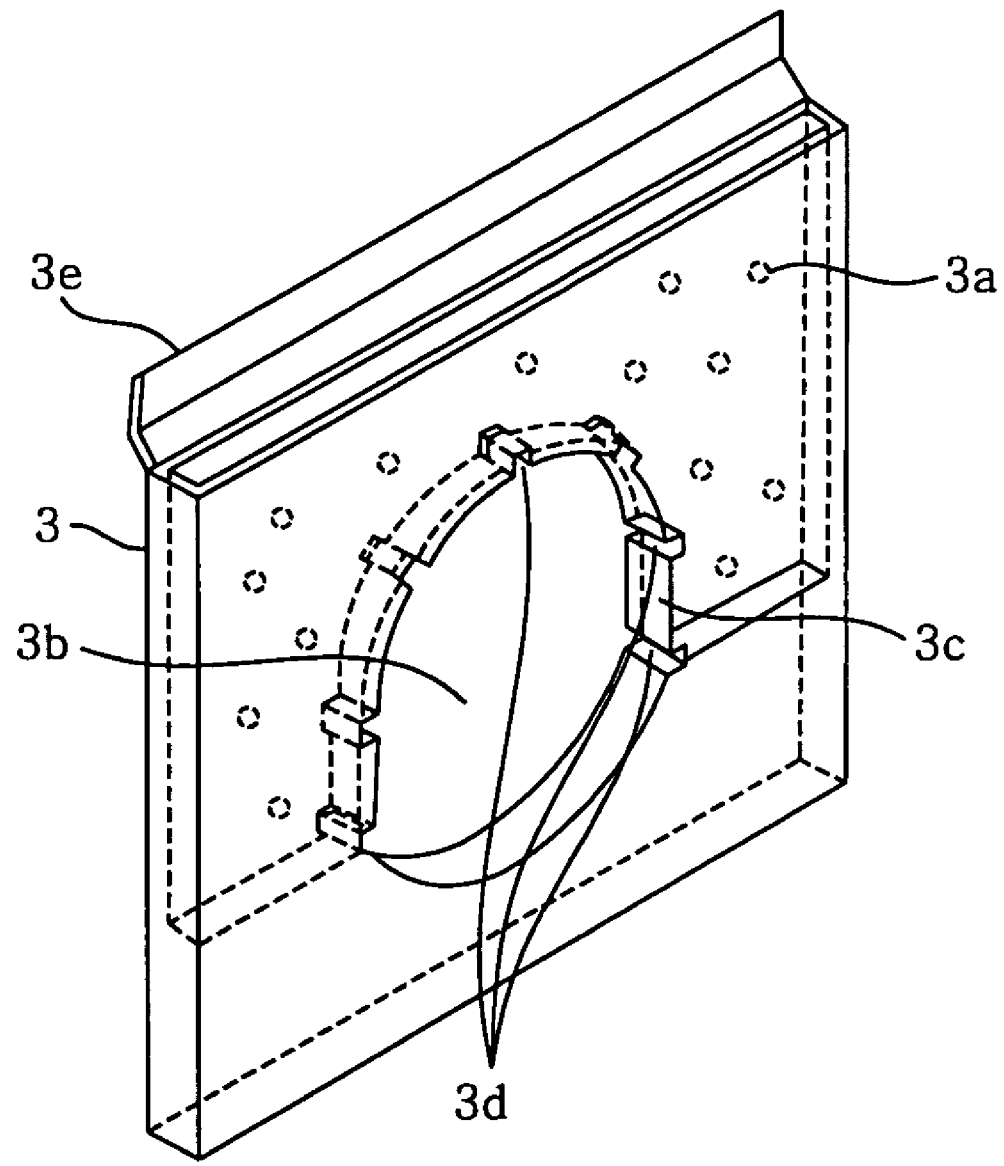
FIG. 2 shows a perspective view showing a storage case of the dust bag in accordance with the first preferred embodiment.
Figure 3:
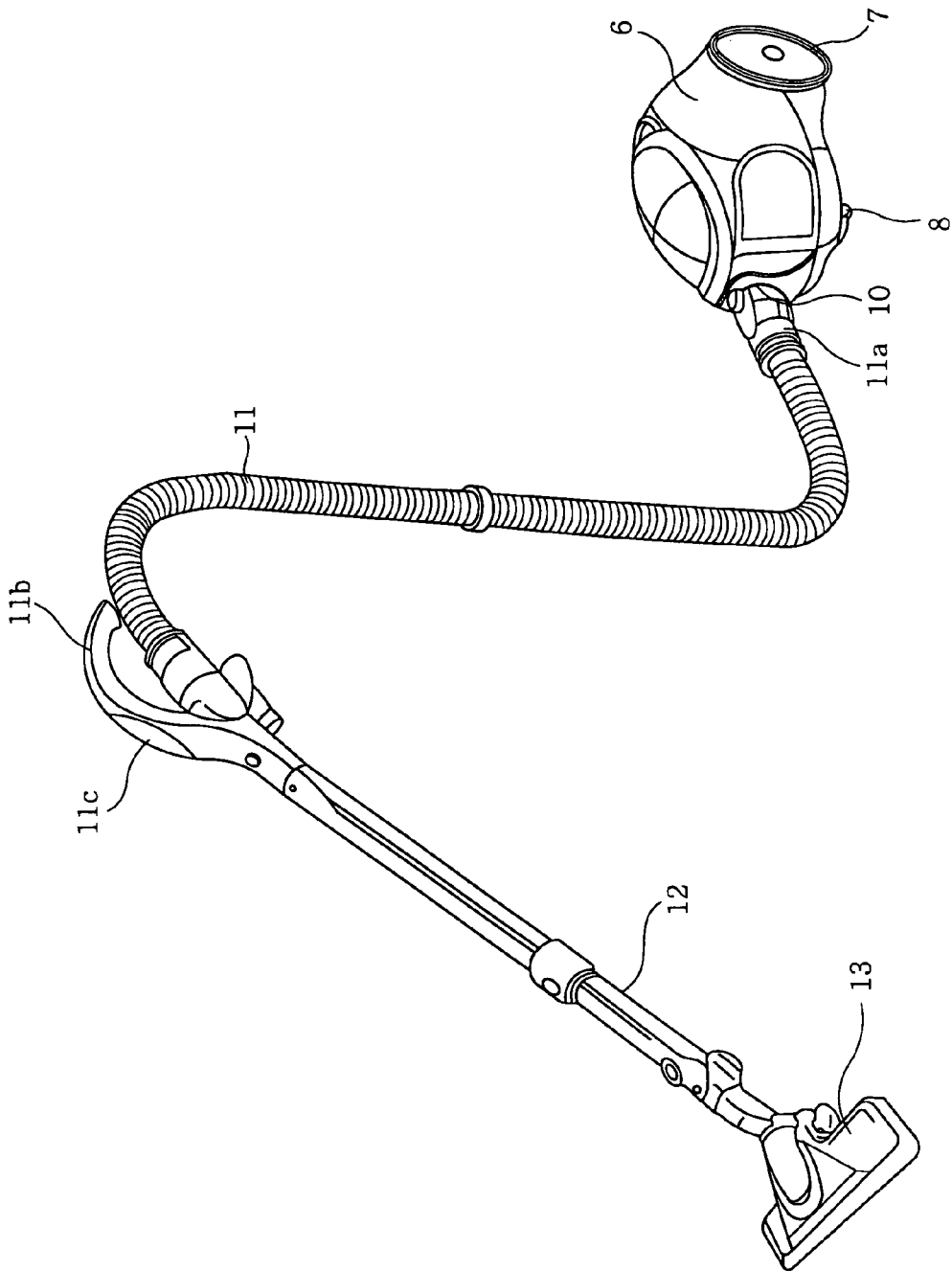
FIG. 3 sets forth an overall perspective view showing the vacuum cleaner equipped with the dust bag in accordance with the first preferred embodiment.
Figure 4:
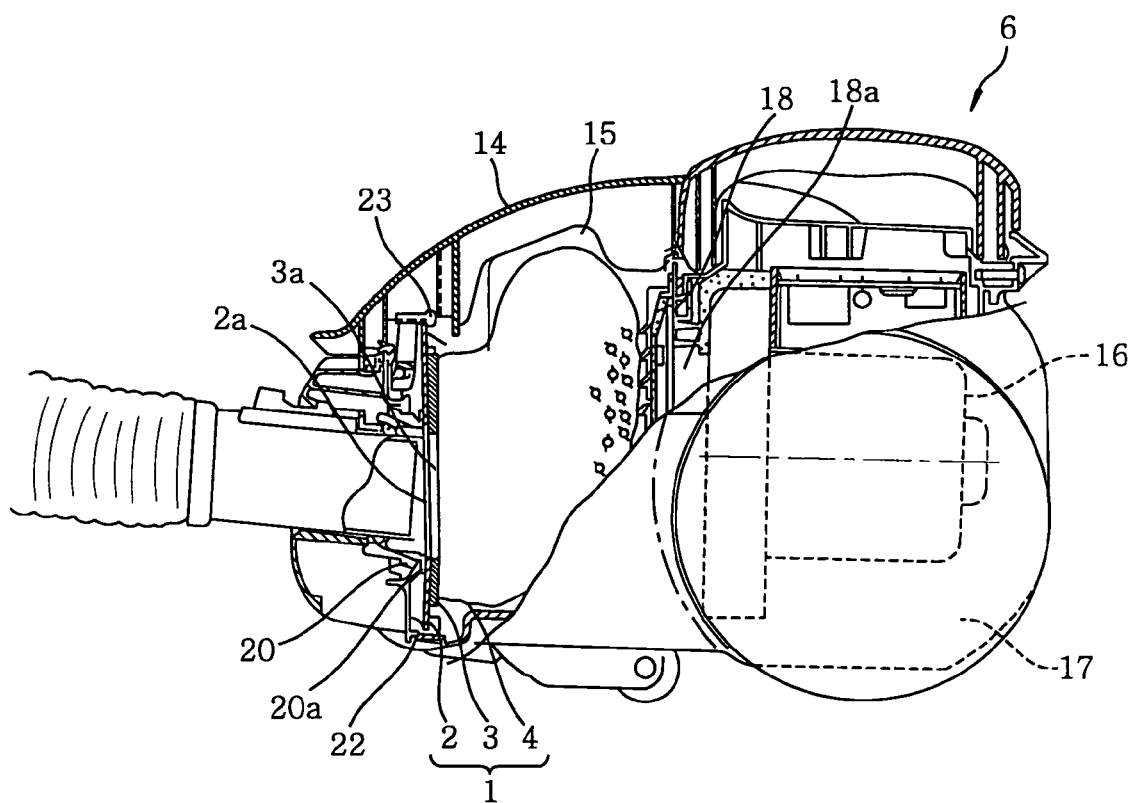
FIG. 4 offers a cross sectional view showing a main body of the vacuum cleaner in accordance with the first preferred embodiment.
Figure 5:
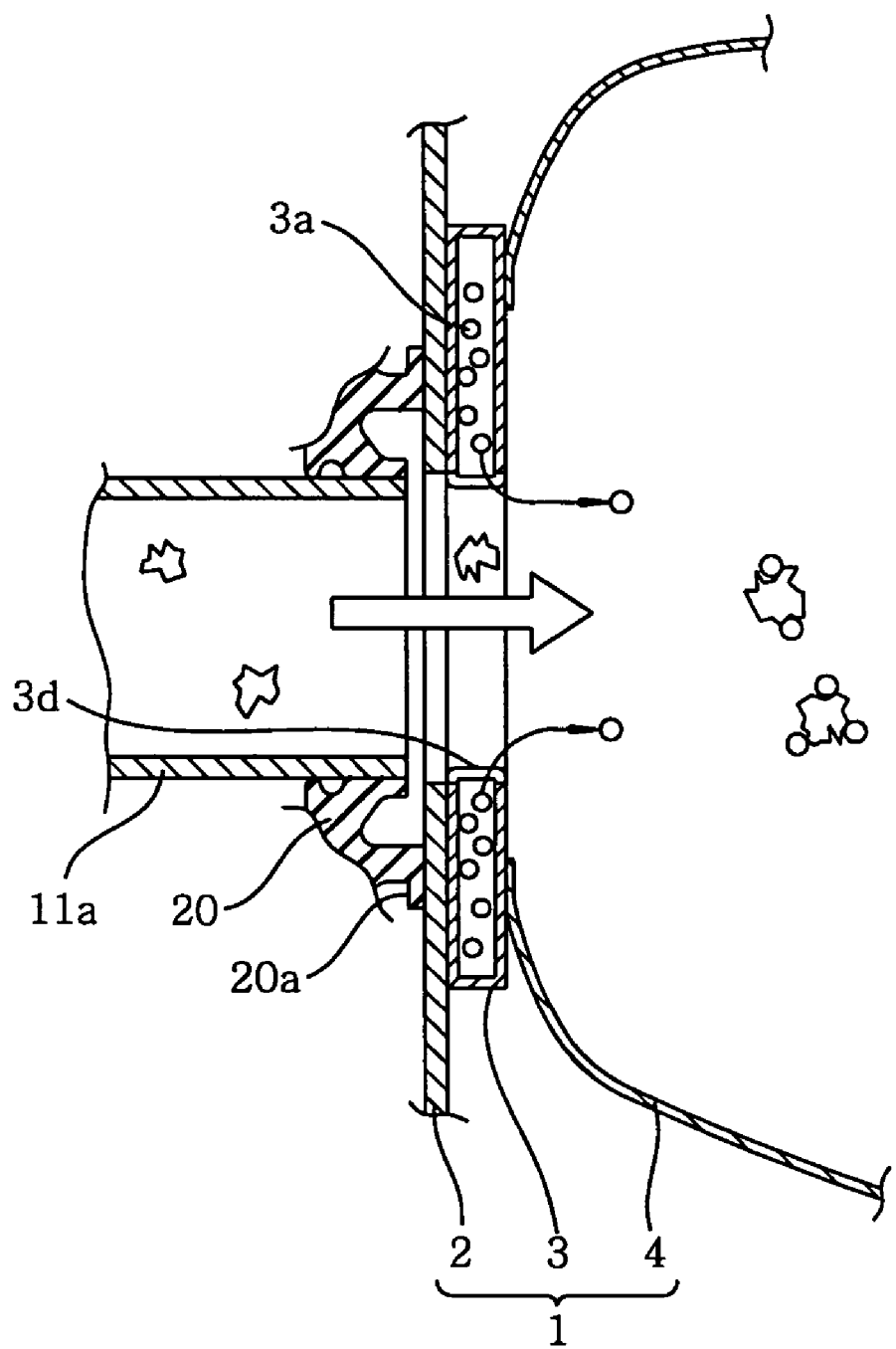
FIG. 5 provides a cross sectional view showing main parts of the vacuum cleaner in accordance with the first preferred embodiment.

FIG. 1 is an exploded perspective view showing a dust bag for a vacuum cleaner in accordance with a first preferred embodiment of the present invention; FIG. 2 shows a perspective view showing a storage case of the dust bag; FIG. 3 sets forth an overall perspective view showing the vacuum cleaner equipped with the dust bag; FIG. 4 offers a cross sectional view showing a main body of the vacuum cleaner; and FIG. 5 provides a cross sectional view showing main parts of the vacuum cleaner.

Referring to FIG. 1, dust bag 1 for a vacuum cleaner in accordance with a first preferred embodiment of the present invention includes core 2 made of paper or resin and provided with opening 2a for suction of dust and dirt; storage case 3, fixed to a rear surface of core 2, (i.e. a surface positioned downstream of the suction air flow when it being mounted on the vacuum cleaner) containing deodorant 3a of the granule or powder shape; and envelope-shaped body 4 provided with suction port 4a for suction of dust and dirt on the front surface thereof and made of a filtering material, e.g., paper or fabric, shaping them into an envelope shape. In accordance with the first preferred embodiment, envelope-shaped body 4 is made of paper and is glued to the rear surface of storage case 3.

Referring to FIG. 2, storage case 3 has opening 3b therein; inner peripheral surface 3c formed in a direction parallel to a suction air flow from opening 2a of the core 2 to form opening 3b; and discharge ports 3d, formed on inner peripheral surface 3c, for communicating an inside of storage case 3 with opening 3b to discharge deodorant 3a contained in storage case 3 therethrough. Further, cover 3e is disposed on an upper end of storage case 3 to seal it after deodorant 3a is added into storage case 3 (in FIG. 2, cover 3e is shown in an open state).

When dust bag 1 is assembled, opening 2a of core 2, opening 3b of storage case 3 and suction port 4a of envelope-shaped body 4 must be aligned so as to communicate with one another, as will be obvious to those skilled in the art.

In the first preferred embodiment, 5 g of powdery hydrophobic zeolite having a mean granule diameter of 5 μm is filled as deodorant 3a in storage case 3.

The vacuum cleaner in accordance with the first preferred embodiment will now be described with reference to FIG. 3.

Main body 6 of the vacuum cleaner has a pair of rear wheels 7, disposed on a rear portion thereof, for rolling and front swivel caster 8 provided on a front portion thereof for rolling. Main body 6 has suction inlet 10 formed on the front surface thereof, which communicates with the dust chamber described later. Hose 11 has connection pipe 11a on one end thereof to be connected to suction inlet 10 and leading pipe 11b on the other end thereof to be used in manipulating during an operation of the vacuum cleaner. Further, leading pipe 11b is connected to suction head 13 for floor cleaning via extension tube 12.

As shown in FIG. 4, main body 6 of the vacuum cleaner includes dust chamber 15 provided in a front portion thereof in such a manner that it can be freely opened and closed with dust collection cover 14 to freely mount dust bag 1 therein; electric blower chamber 17 disposed on a rear portion thereof to accommodate therein electric blower 16 for generating the suction air flow; and a discharge port (not shown) positioned on a rear surface thereof so that electric blower chamber 17 communicates with the outside and air is discharged from the electric blower 16. Reference numeral 18 represents a partition wall for partitioning dust chamber 15 and electric blower chamber 17. Partition wall 18 is provided with opening 18a in a lattice shape through which dust chamber 15 and electric blower 17 communicate with each other.

Packing 20 is provided on a rear end of the suction inlet 10 disposed on a front portion of main body 6. Packing 20 is made of an elastic material, such as rubber, vinyl chloride, or silicone, and has a ring-shaped lip 20a on a rear portion thereof.

In the first preferred embodiment, dust bag 1 is mounted on main body 6 such that the lower end of core 2 of dust bag 1 is inserted into groove portion 22 formed on a bottom of main body 6 and the upper end of core 2 is hung on hook 23 provided in main body 6, wherein hook 23 can make a small movement freely. Lip 20a of packing 20 is pressed against the periphery of opening 2a of core 2 while core 2 is fastened at a predetermined position, thereby maintaining an airtight state.

The operation of the vacuum cleaner equipped with dust bag 1 in accordance with the first preferred embodiment will now be described.

An electric cord (not shown) drawn from main body 6 of the vacuum cleaner is plugged into a wall socket (not shown) Switch 11c provided on leading pipe 11b is operated to start electric blower 16. The resulting suction force draws dust and dirt from the floor surface together with the air nearby through a suction port (not shown) formed on the bottom surface of suction head 13, via hose 11 and extension tube 12.

The air drawn via the suction port of suction head 13 forms a suction air flow to pass through extension tube 12, hose 11 and suction inlet 10 together with the dust and dirt. The suction air flow further travels through opening 2a of core 2, opening 3b of storage case 3 and suction port 4a of envelope-shaped body 4 to enter the envelope-shaped body 4. After the dust and dirt are caught and collected in the envelope-shaped body 4, cleansed air is discharged to the outside via electric blower 16 and the discharge port.

Further, when the suction air flow passes through opening 3b of storage case 3 together with the dust and dirt, as shown in FIG. 5, a suction force due to an ejector effect acts on the inside of storage case 3 via discharge ports 3d. As a result, deodorant 3a of the granule or powder shape, which is contained in storage case 3, is released and mixed with the dust and dirt. The mixture enters into envelope-shaped body 4 and is accumulated therein starting from the innermost part thereof (a part near electric blower 16).

On a microscopic scale, since the outer periphery of each dust and dirt is surrounded by deodorant 3a of the granule or powder shape, the contact area of deodorant 3a with the dust and dirt is substantially large and the dust and dirt remain surrounded by deodorant 3a inside dust bag 1. As a result, deodorant 3a works extremely effectively to reduce the odor to a substantial degree.

In addition, deodorant 3a remains to be kept together with the dust and dirt until dust bag 1 is thrown away or envelope-shaped body 4 is emptied. Accordingly, the deodorizing effect is excellent and continues to work for a long period of time to thereby make the vacuum cleaning pleasant.

Furthermore, since the diameter of the granule or powder of deodorant 3a is larger than that of pores of envelope-shaped body 4, through which air permeates (i.e. a gap between fibers of paper or fabric constituting envelope-shaped body 4), deodorant 3a drawn together with the dust and dirt is prevented from passing through the pores of envelope-shaped body 4 to thereby maintain the deodorizing effect for a long period of time.

(Experiment 1)

An experiment for investigating the effect of the present invention was performed by using the vacuum cleaner having the above-mentioned configuration.

The vacuum cleaner was used to clean a room for fifteen minutes, once a day. As a comparative experiment, a room of the same size was cleaned for fifteen minutes a day with a vacuum cleaner having no deodorant 3a. These cleaning experiments had been conducted for thirty days while careful attention had been paid on the odor from discharged air. The results showed that, in case of the comparative experiment, strong odor had been sensed from the discharged air since about seventh day, but little odor had been sensed until the final day of the experiment in case of the vacuum cleaner in accordance with the preferred embodiment.

The amounts of the dust and dirt collected by the vacuum cleaners for thirty days were compared to be found that they were about 150 g in both cases. Further, the amount of deodorant 3a in storage case 3 was reduced by about 1.5 g. Accordingly, on an average, 5 g of dust and dirt were collected and 0.05 g of deodorant 3a were discharged from storage case 3 by the suction air flow for each cleaning.

A close observation of the collected dust and dirt showed that deodorant 3a were attached to the dust and dirt such that the dust and dirt were coated with deodorant 3a of the powder shape.

After the vacuum cleaners were left undisturbed for a day with the dust and dirt of 150 g collected, the vacuum cleaners were operated for sixty seconds in a closed chamber of a 1 m$^3$ size. Six sensory evaluation panelists, including both males and females, smelled the air in the chamber to evaluate the odor strength in six levels (0-5th level), wherein level 0 represents no smell (absence of perceptible smell); level 1, very weak smell (which can't be defined); level 2, weak smell (which doesn't attract attention but can be identified if you pay attention to it; level 3, noticeable smell (which can be easily identified); level 4, distinct smell (which engages attention); and level 5, very strong smell).

The results showed that, on an average, the odor strength was evaluated to be 0.8 in case of the vacuum cleaner in accordance with the preferred embodiment, while the odor strength was evaluated to be 3.4 in case of the comparative experiment, which shows a substantial reduction effect of odor.

It is obvious from the experiments described above that the vacuum cleaner in accordance with the first preferred embodiment can substantially remove odor from dust and dirt since deodorant 3a is discharged from storage case 3 into envelope-shaped body 4 by the suction air flow so that the dust and dirt are coated with deodorant 3a. After the vacuum cleaner had been used, deodorant 3a keeps carrying out the deodorizing performance even while the vacuum cleaner is left undisturbed. As a result, far less odor remains inside envelope-shaped body 4. In particular, it is possible to reduce the odor of the discharged air even in the initial period of use of a vacuum cleaner while the level of odor is high.

Although hydrophobic zeolite is used as a deodorant in the first preferred embodiment, active carbon or transition metal oxide instead of the hydrophobic zeolite can also be used to reduce the complex odor from dust and dirt collected by the vacuum cleaner to the same degree.

(Experiment 2)

A second experiment was performed to evaluate the effect of the vacuum cleaner in accordance with the present invention.

The second experiment was to investigate the relationship between the amount of powdery deodorant 3a injected into envelope-shaped body 4 and the deodorizing effect on discharged air for the vacuum cleaner in accordance with the first preferred embodiment.

In Experiment 2, dust and dirt including hair of pets of a strong odor were compared with dust and dirt from a house having no pet. The same panelists as in Experiment 1 smelled the odor of air discharged from the vacuum cleaners, which had drawn dust and dirt of 100 g for both cases, while varying the operation time of electric blower 16 and the total amount of discharged deodorant 3a.

Figure 6:
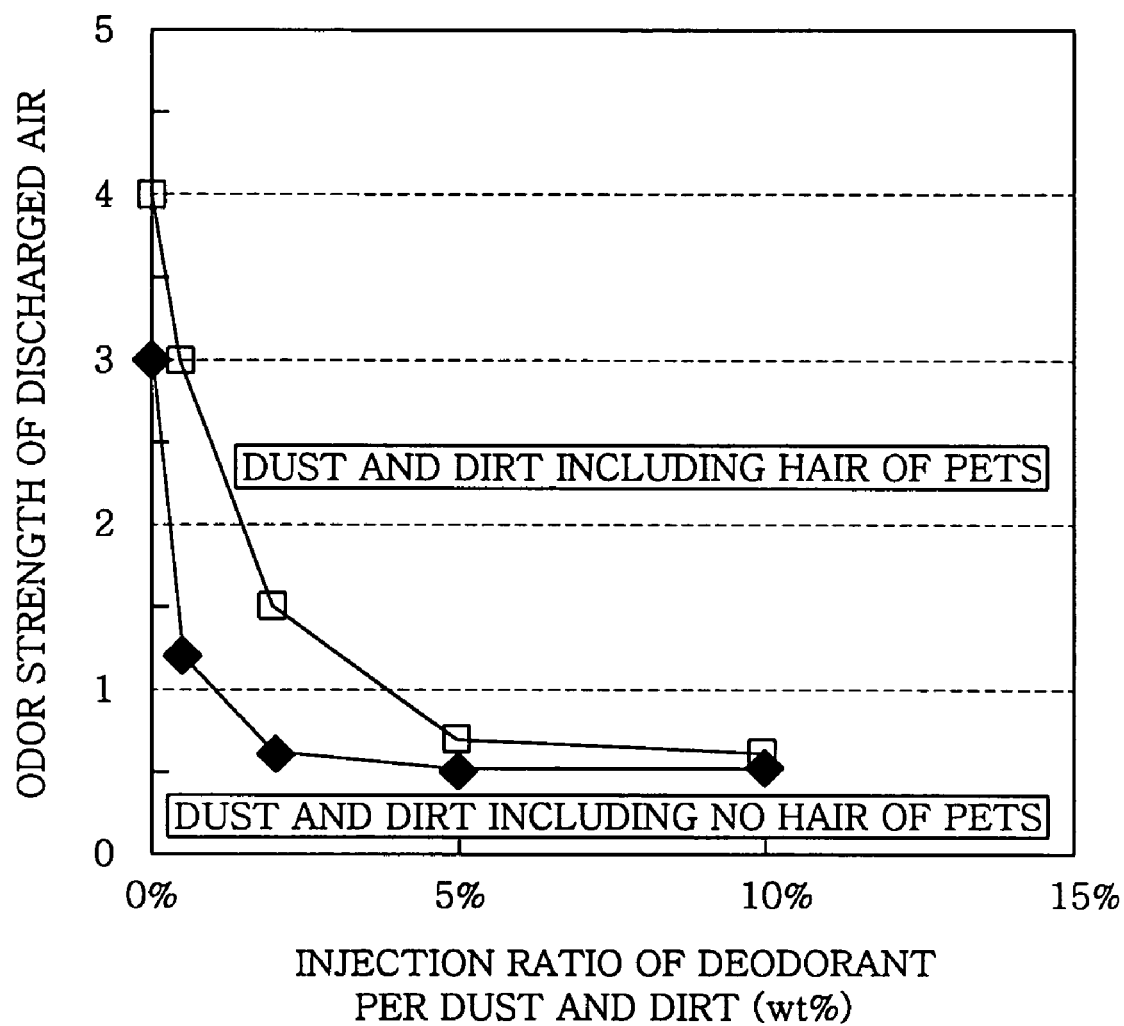
FIG. 6 is a graph showing a relationship between an injection ratio of a deodorant and an odor strength of discharged air in accordance with the first preferred embodiment.

The relationship between the injection ratio of deodorant 3a per the amount of dust and dirt and the odor strength of discharged air is given in FIG. 6. It is clear from FIG. 6 that, by setting the injection ratio of deodorant 3a within a weight ratio ranging from about 0.5 wt % to 5 wt % in terms of weight ratio relative to the amount of dust and dirt, a sufficient deodorizing effect can be obtained even in case of the dust and dirt including hair of pets of a strong odor.

(Experiment 3)

A third experiment was performed to evaluate the effect of the vacuum cleaner in accordance with the present invention.

Instead of the hydrophobic zeolite having a mean granule diameter of 5 μm in accordance with the first preferred embodiment, another hydrophobic zeolite having various mean granule diameters ranging from about 0.05 μm to about 5 mm was prepared as deodorant 3a, in Experiment 3. Other conditions were the same as in Experiment 1. In addition, the weight of absorbed deodorant was measured.

Figure 7:
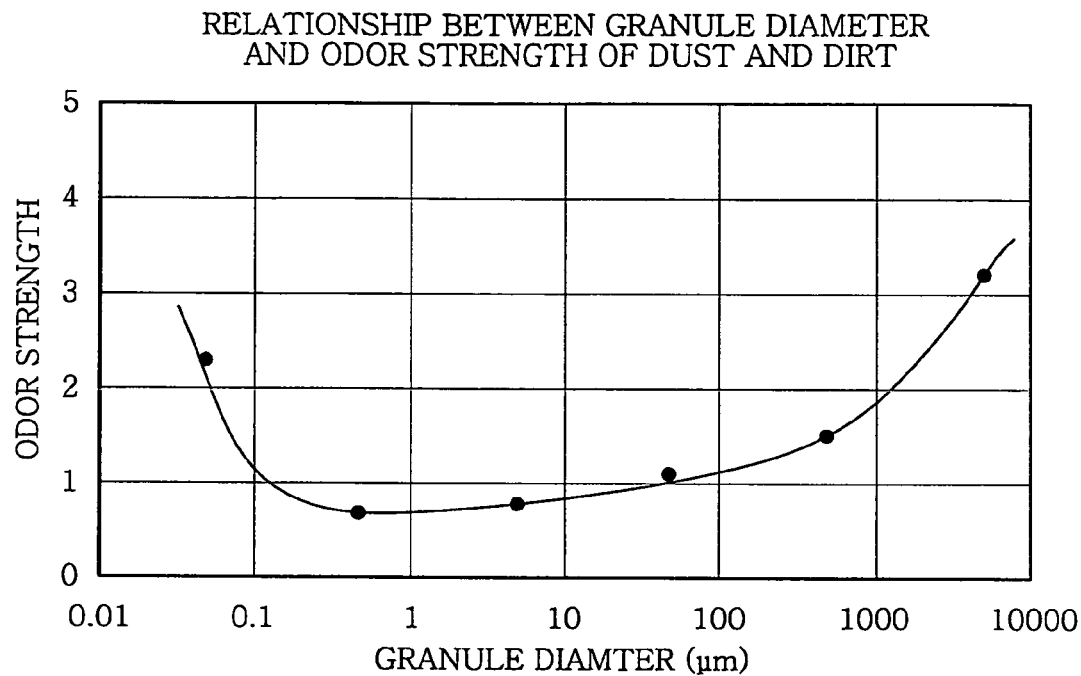
FIG. 7 is an experimental graph showing a relationship between a granule diameter of the deodorant and the odor strength in accordance with the first preferred embodiment.
Figure 8:
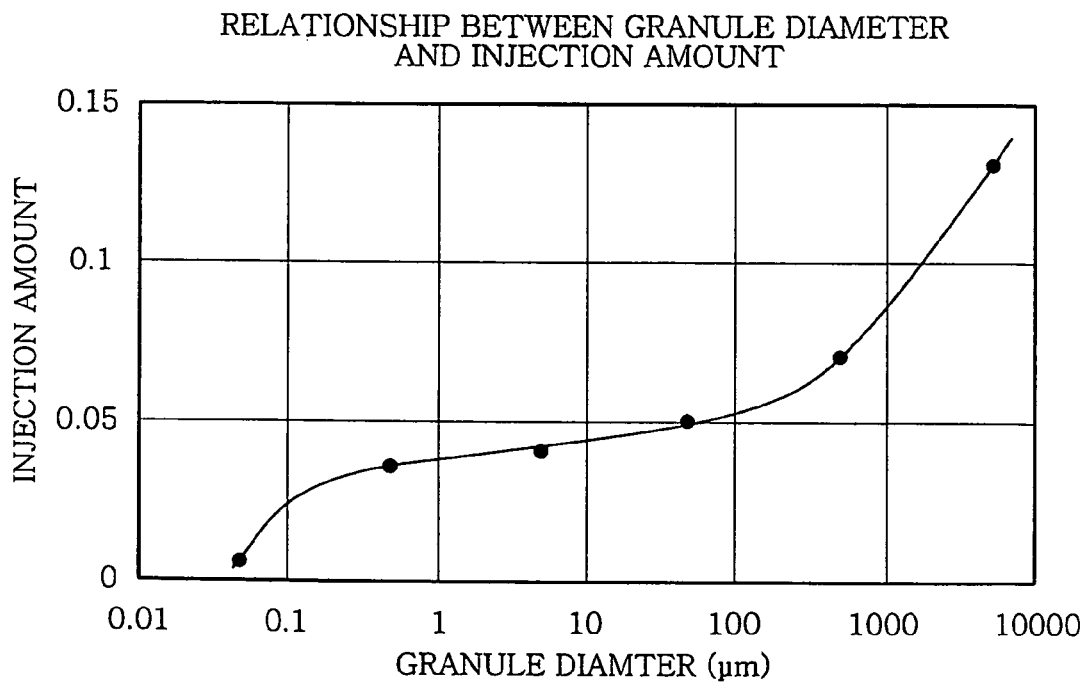
FIG. 8 is an experimental graph showing a relationship between the granule diameter and an injection amount of the deodorant in accordance with a first preferred embodiment.

The relationship between the granule diameter and the odor strength is given in FIG. 7, and the relationship between the granule diameter and the amount of absorbed deodorant is given in FIG. 8.

As shown in FIG. 7, the relationship between the granule diameter and the odor strength is plotted as a downwardly convex curve. As shown in FIG. 8, the amount of absorbed deodorant increases monotonously while the granule diameter is within the range from about 1 μm to about 100 μm, but it decreases abruptly when the granule diameter is smaller than 0.1 μm.

It is clear from the above that, even when the granule diameter is large, a large opening area of discharge port 3d of storage case 3 guarantees sufficient injection of deodorant into envelope-shaped body 4. However, if the granule diameter is larger than 1 mm, deodorant 3a cannot fully cover the surface of dust and dirt. In addition, the surface area of deodorant 3a for adsorbing odorous components decreases in comparison to that of a small diameter of the same weight, thereby deteriorating the deodorizing effect.

When the granule diameter is small, slipping properties among particles are poor. In other words, the fluidity is degraded. Accordingly, it is difficult to smoothly inject deodorant 3a even when discharge port 3d of storage case 3 has a large opening area.

For these reasons, granule diameter of deodorant 3a in the range from about 0.1 μm to 1 mm is optimal to smoothly inject deodorant 3a into envelope-shaped body 4 and realize a vacuum cleaner having an excellent deodorizing effect.

The reason the preferred embodiment has an excellent effect of reducing odor is as follows: an innumerable particles of deodorant 3a are discharged from discharge ports 3d of storage case 3 to be attached to the periphery of each dust and dirt, thereby increasing the contact area of the deodorant with dust and dirt and providing an excellent deodorizing performance, accordingly. In addition, deodorant 3a remains mixed with the dust and dirt and, overall, continuously deodorizes them. In accordance with the present invention, the size of discharge port 3d of storage case 3 is set to be sufficiently larger than the granule diameter of deodorant 3a, and the air-permeable diameter (pore size) of envelope-shaped body 4 having air-permeable properties is configured in advance to be smaller than the granule diameter of deodorant 3a. Further, it is important that deodorant 3a remains in envelope-shaped body 4 without leaking, even while electric blower 16 generates vibration during suction of dust and dirt. This applies to every embodiment and experiment to be described later.

The preferred embodiment is also advantageous in that, since storage case 3 is provided downstream from core 2, dust bag 1 is applicable to a conventional vacuum cleaner having a dust bag without storage case 3. Accordingly, the compatibility can be improved and the manufacturing or the inventory management of dust bag 1 may be simplified.

Since each of core 2, storage case 3 and envelope-shaped body 4 is made of a flammable material, dust bag 1 can be thrown away in an easy and sanitary manner by simply burning it without being separated from other wastes.

In addition, in case paper is used as the flammable material, the cost of material is reduced and a forming die is unnecessary, thereby improving the mass productivity and substantially reducing the total cost.

As storage case 3 includes discharge ports 3*d* formed on the surface parallel to the air flow, deodorant 3*a* of the granule or powder shape is discharged from discharge ports 3*d* in a continuous and efficient manner by means of the suction performance resulting from the ejector effect of the suction air flow, which guarantees an excellent deodorizing effect. The ejector effect varies depending on the speed of the suction air flow. That is, the ejector effect is proportional to the strength of the suction air flow (i.e. amount of the collected dust and dirt). As a result, the amount of injected deodorant 3*a* is automatically adjusted in conformity with the amount of the collected dust and dirt, which guarantees an excellent deodorizing effect without wasting deodorant 3*a*.

Although envelope-shaped body 4 is glued to the rear surface of storage case 3 in accordance with the first preferred embodiment, it may also be glued to the rear surface of core 2, considering the cost or convenience of assembly of dust bag 1.

Although envelope-shaped body 4 is made of paper in accordance with the first preferred embodiment, it may also be made of fabric and have a disposal port (not shown) capable of being opened and closed freely to throw away dust and dirt by providing the disposal port on a downstream end. In case envelope-shaped body 4 is full of dust and dirt, the disposal port is opened to remove the dust and dirt from inside thereof and envelope-shaped body 4 is then reusable. Preferably, cover 3*e* of storage case 3 can be opened and closed freely so that the user can supplement deodorant 3*a* as desired, because storage case 3 must be refilled with deodorant 3*a* every time dust and dirt are thrown away or after several times of disposal. Further, in case storage case 3 is made of a transparent or translucent material, the amount of deodorant 3*a* remaining therein can be checked easily from outside, thereby preventing deodorant 3*a* from running out during an operation of the vacuum cleaner and improving the user's efficiency.

Furthermore, a light-emitting device (not shown) and a light-receiving device (not shown) may be respectively installed in the front and rear of a portion of storage case 3 containing deodorant 3*a* to face each other in case storage case 3 is made of a transparent or translucent material as mentioned above. In this case, since the amount of remaining deodorant 3*a* is automatically detected if the amount is below an allowable level, the user is informed of it by means of sound, light or vibration, thereby improving the user's efficiency Second Preferred Embodiment FIGS. 9A and 9B offer a perspective view and major parts of a dust bag for a vacuum cleaner in accordance with a second preferred embodiment of the present invention, respectively. Here, parts identical to those described in the first preferred embodiment will be assigned same reference numerals, and description thereof will be omitted.

Figure 9A:
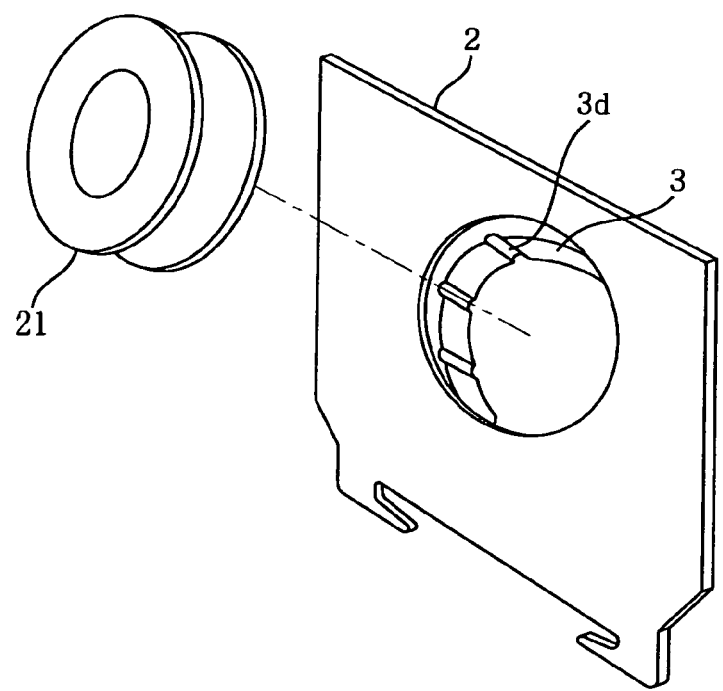
FIG. 9A sets forth a perspective view showing a dust bag for a vacuum cleaner in accordance with a second preferred embodiment of the present invention.
Figure 9B:
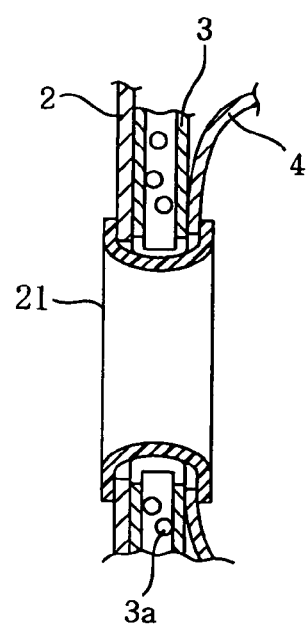
FIG. 9B shows a cross sectional view showing major parts of the dust bag for the vacuum cleaner in accordance with the second preferred embodiment.

In accordance with a second preferred embodiment, cover member 21 of a ring shape, made of resilient material, such as rubber, silicone or resin having an elastic restoration force, covers discharge ports 3*d* of storage case 3 as shown in FIGS. 9A and 9B, in case of packing dust bag 1. Accordingly, dust bag 1 can be carried without leaking deodorant 3*a* from storage case 3, thereby reducing the inconvenience of the user while using dust bag 1.

Further, since cover member 21 is made of resilient material and formed in a ring shape, it becomes easy to attach and detach cover member 21 to and from discharge ports 3*d*, thereby improving the effect of sealing discharge ports 3*d* without deteriorating the deodorizing effect of deodorant 3*a* in storage case 3 while dust bag 1 is stored.

Moreover, although cover member 21 has a ring shape in this embodiment, any other shape of cover member 21 may be used as long as it covers discharge ports 3*d*. For example, cover member 21 may have a U-shape or the like. Solidification of deodorant 3*a* caused by moisture is prevented by improving the sealing effect of cover member 21 for sealing discharge ports 3*d*. Accordingly, deodorant 3*a* can be of the granule or powder shape for a long period of time.

Third Preferred Embodiment

A third embodiment of the present invention will now be described.

In the third preferred embodiment, powdery silica gel is added to hydrophobic zeolite, used as a deodorant in the first preferred embodiment, at a ratio of 10%.

Since the silica gel has a strong hygroscopic effect, germs attached to dust and dirt are prevented from multiplying in case of being injected into dust bag 1.

The silica gel also absorbs moisture inside storage case 3, and prevents deodorant 3*a* from absorbing moisture and losing fluidity, which guarantees a long-term injection of deodorant 3*a* into envelope-shaped body 4.

Although silica gel is used as the hygroscopic material in the second preferred embodiment, alumina or non-hydrophobic zeolite also has a strong hygroscopic effect and exhibits the same effect.

Fourth Preferred Embodiment

A fourth preferred embodiment of the present invention will now be described.

In the fourth preferred embodiment, ultra-fine silicic anhydride having a mean granule diameter of 0.01 μm or less is added to hydrophobic zeolite, used as a deodorant in the first preferred embodiment, at a ratio of 1%.

The silicic anhydride has excellent sliding properties and prevents deodorant 3*a* from losing fluidity when filling storage case 3. In addition, clogging of storage case 3 is avoided, thereby guaranteeing a long-term injection of deodorant 3*a* into envelope-shaped body 4.

Although silicic anhydride is used as the material for improving fluidity in the fourth preferred embodiment, any other material may be used as long as it has excellent sliding properties and improves the fluidity of a powder type.

Fifth Preferred Embodiment

A fifth preferred embodiment of the present invention will now be described.

In the fifth preferred embodiment, alumina including 1% of silver is added to hydrophobic zeolite, used as a deodorant in the first preferred embodiment, at a ratio of 5%.

In case the silver is injected into envelope-shaped body 4 together with deodorant 3*a* contained in storage case 3, since the silver has excellent antibacterial properties, germs attached to dust and dirt are prevented from multiplying, thereby suppressing the generation of odor and providing an excellent deodorizing effect.

Although silver is used as the antibacterial material in the fifth preferred embodiment, zinc also has excellent antibacterial properties and exhibits the same effect.

Sixth Preferred Embodiment

A sixth preferred embodiment of the present invention will now be described.

In the sixth preferred embodiment, essential oil of a herb as vegetable oil is added to hydrophobic zeolite, used as a deodorant in the first preferred embodiment, at a ratio of 0.1%.

The vegetable oil emits fragrance so that it is added to the discharged air deodorized by hydrophobic zeolite, for pleasant environments.

Although vegetable oil extracted from plants is used as the aromatic material in the sixth preferred embodiment, a chemical aromatic, such as ether, also exhibits the same effect.

Seventh Preferred Embodiment

A seventh preferred embodiment of the present invention will now be described.

Figure 10:
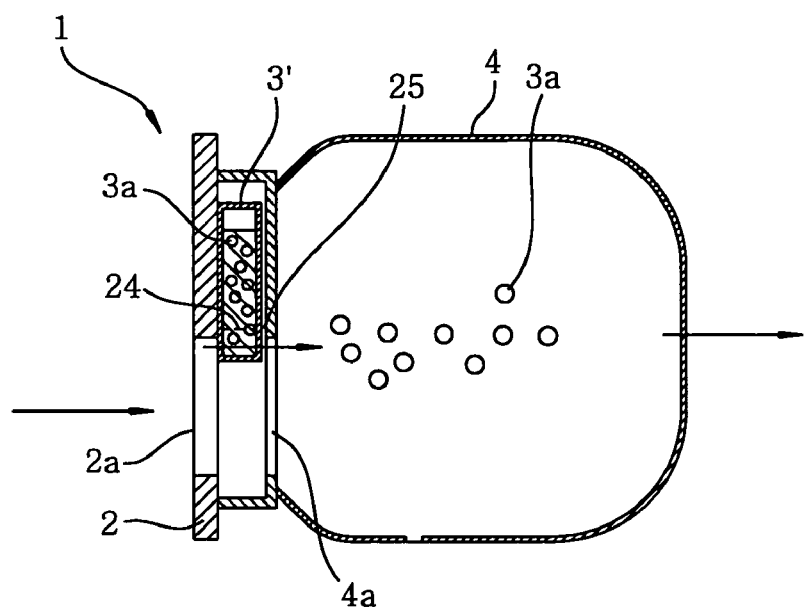
FIG. 10 offers a cross sectional view briefly showing a dust bag for a vacuum cleaner in accordance with a seventh preferred embodiment of the present invention.
Figure 11:
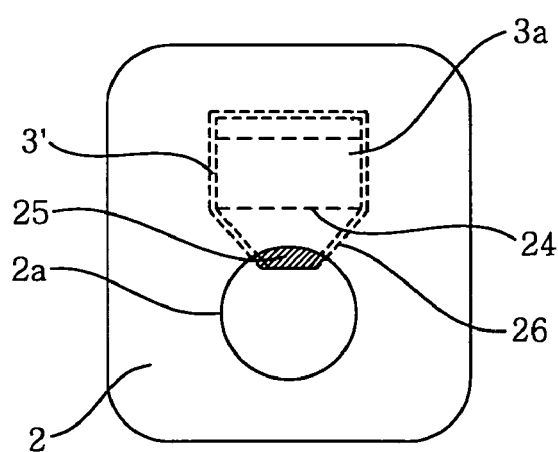
FIG. 11 illustrates a front view briefly showing the dust bag in accordance with the seventh embodiment.

FIG. 10 offers a cross sectional view briefly showing a dust bag for a vacuum cleaner in accordance with the seventh preferred embodiment of the present invention, and FIG. 11 shows a front view briefly showing the same dust bag.

Referring to FIGS. 10 and 11, dust bag 1 includes storage case 3' made of acrylic and filled with deodorant 3a; air-permeable envelope 25 fastened to storage case 3' while covering opening end 24 of storage case 3'; air-permeable envelope-shaped body 4 for filtering and collecting drawn dust and dirt; and core 2 provided with opening 2a to be mounted on the vacuum cleaner. A part of the air-permeable envelope 25 is protruded into opening 2a of core 2. Air-permeable envelope 25 is manufactured by forming a sheet of non-woven fabric into an envelope shape, air-permeable envelope 25 having a nominal size of 30 g/m² and a thickness of 0.2 mm.

Further, air-permeable envelope 25 has a tapered shape whose horizontal cross sectional area gradually decreases toward opening 2a of core 2.

Instead of the non-woven fabric, air-permeable envelope 25 may be made of another air-permeable material which is subject to a punching process.

The operation of the vacuum cleaner equipped with dust bag 1 in accordance with the seventh preferred embodiment will now be described.

An air flow is introduced via opening 2a of core 2 together with dust and dirt and, then, the dust and dirt are filtered and collected by envelope-shaped body 4. A part of the air flow introduced via opening 2a of core 2 collides with air-permeable envelope 25 protruded into opening 2a and is directed toward the inside of air-permeable envelope 25. Then, the part of the air flow extrudes deodorant 3a contained in air-permeable envelope 25 through the space between strands of air-permeable envelope 25, so that deodorant 3a is injected into envelope-shaped body 4.

Deodorant 3a in a region protruding into opening 2a of core 2 collides with the air flow and is discharged to thereby leave an empty space in the protruding region. Deodorant 3a remaining in storage case 3' sinks, due to gravity, toward opening 2a along taper 26 of air-permeable envelope 25 due to a vibration or an impact resulting from a movement of main body 6 of the vacuum cleaner to fill the empty space. Such processes are repeated so that deodorant 3a contained in storage case 3 always sinks, due to gravity, toward opening 2a along taper 26 of air-permeable envelope 25 to fill the empty space.

Further, deodorant 3a thus injected into envelope-shaped body 4 is uniformly attached to the surface or inside of dust and dirt to adsorb the odor from the dust and dirt. This substantially reduces the odor included in discharged air during the operation of the vacuum cleaner.

In accordance with the seventh preferred embodiment, as mentioned above, air-permeable envelope 25 is made of non-woven fabric and has a horizontal cross sectional area gradually decreasing toward opening 2a of core 2 (i.e. has a tapered shape). By disposing air-permeable envelope 25 in storage case 3', deodorant 3a contained in storage case 3' smoothly sinks, due to gravity, toward opening 2a along taper 26 of air-permeable envelope 25. Further, deodorant 3a can be stably injected toward the dust and dirt inside envelope-shaped body 4.

Although a sheet of air-permeable material is shaped into an envelope shape to form air-permeable envelope 25 fastened to storage case 3' in the seventh preferred embodiment, air-permeable envelope 25 may be formed by laminating a plurality of sheets of air-permeable material and shaping them into an envelope shape. In this case, the strength of the air-permeable envelope is superior to the case of using a single sheet. Furthermore, by laminating the sheets of material, air passages can be made to be misaligned with one another, thereby reducing the air-permeable diameter even when materials of the same air-permeable diameter are used. As a result, the amount of injected deodorant 3a can be adjusted accordingly.

In addition, thick paper may be subjected to a pressing process to form air-permeable holes thereon and assembled from a development figure into a box to be used as an air-permeable portion. Materials having no air-permeable properties can be used to easily manufacture an air-permeable portion, which enables stable injection of deodorant 3a. The amount of injected deodorant 3a can be adjusted by selecting a desired size of the air-permeable holes during the pressing process. Alternatively, plastic may be subjected to injection molding to shape an air-permeable box having air-permeable holes formed thereon and the air-permeable box may be used as the air-permeable portion. In this case, a process for forming the air-permeable holes is omitted, and the manufacturing process is simplified accordingly.

Eighth Preferred Embodiment

Figure 12:
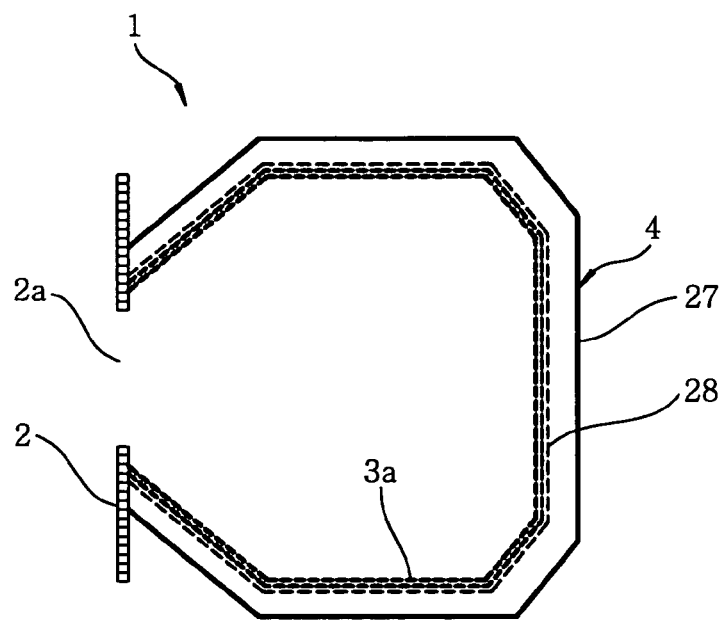
FIG. 12 shows a cross sectional view briefly showing a dust bag for a vacuum cleaner in accordance with an eighth preferred embodiment of the present invention.

FIG. 12 provides a cross sectional view briefly showing a dust bag for a vacuum cleaner in accordance with an eighth preferred embodiment of the present invention.

As shown in FIG. 12, dust bag 1 includes core 2 provided with an opening for suction of dust and dirt and made of paper or resin and envelope-shape body 4 fixed to a rear surface of core 2 (i.e. a surface positioned downstream from the suction air flow when being mounted on the vacuum cleaner). Envelope-shape body 4 is made of a filtering material, e.g., paper, fabric or non-woven fabric and formed by laminating the filtering material in a plurality of layers and forming them into an envelope shape. Further, envelope-shape body 4 has inner envelope 28 and outer envelope 27, and open portion thereof is glued to be installed to core 2.

Deodorant 3a is fixedly attached to the surface of inner envelope 28 via a binder. In order to attach deodorant 3a, slurry is prepared by dispersing 20 weight part of deodorant 3a and 2 weight part of binder into 100 weight part of distilled water. As deodorant 3a, deodorizing powder, such as active carbon, transition metal catalyst or zeolite, may be used. In the eighth preferred embodiment, zeolite 5 is selected. The binder may be an organic or inorganic binder. However, the inorganic binder is preferred because of its excellent thermal stability and weak influence on the performance of the deodorizing powder. Particularly, silica-based inorganic binder is used.

Inner envelope 28 of dust bag 1 is obtained as follows: non-woven fabric is dipped into the slurry having the above-described materials dispersed therein. After the non-woven fabric is taken out of the slurry and dried at 80° C. for eight hours, the fabric is maintained at a higher temperature of 180° C. for two hours. This completes the attachment process of the materials and inner envelope 28 is provided.

Further, if necessary, the dipping and drying processes may be repeated a number of times so that a larger amount of deodorant 3a is attached to the surface of inner envelope 28 in a number of layers. In the eighth preferred embodiment, the attachment process is repeated three times so that inner envelope 28 where deodorant 3a of 5 g is attached to each dust bag is used.

Moreover, in case deodorant 3a attached to inner envelope 28 in the above method is subjected to an impact, for example, when an external impact acts on deodorant 3a, when envelope-shaped body 4 is deformed due to a change in the air flow when the vacuum cleaner is turned on/off, or when the air flow in envelope-shaped body 4 pulsates, the binder collapses, detaches and easily releases deodorant 3a from inner envelope 28. Accordingly, deodorant 3a returns to its original powder state and is attached to dust and dirt.

As a means for causing deodorant 3a to collapse for attachment to dust and dirt, vibrating means may be accommodated in the dust collection chamber 15 of the vacuum cleaner to apply an electric vibration to envelope-shaped body 4. As the vibrating means, a combination of a vibration generator, such as a solenoid, and a vibration transmission plate is preferred, because it can apply the vibration to envelope-shaped body 4 on a large scale. The position to which the vibration is to be applied may be, for example, the rear portion of envelope-shaped body 4. However, the position is not limited thereto, as long as envelope-shaped body 4 can be vibrated properly.

In the above configuration, the binder in inner envelope 28 partially collapses, due to an impact from the suction air flow generated when electric blower 16 is operated or due to a vibration resulting from a movement of main body 6. As a result, deodorant 3a falls toward the dust and dirt, and is uniformly attached thereto under the influence of the air flow. In such manner, the odor resulting from the dust and dirt is adsorbed, and the odor included in the air discharged from the vacuum cleaner is reduced, thereby realizing pleasant cleaning environment.

Ninth Preferred Embodiment

Figure 13:
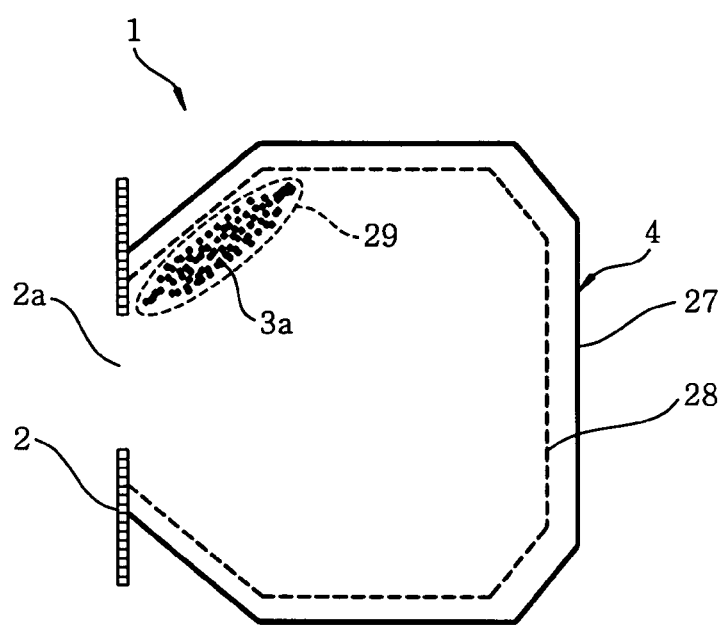
FIG. 13 is a cross sectional view briefly showing a dust bag for a vacuum cleaner in accordance with a ninth preferred embodiment of the present invention.

FIG. 13 is a cross sectional view briefly showing a dust bag for a vacuum cleaner in accordance with an ninth preferred embodiment of the present invention.

As shown in FIG. 13, reference numeral 29 refers to an air-permeable envelope formed by processing resin-based fibers into an envelope shape. After deodorant 3a is put into air-permeable envelope 29, an opening end thereof is then sealed. Air-permeable envelope 29 has a space between strands of 50-100 μm so that deodorant 3a hardly leaks in a static state and is discharged in an appropriate quantity in case of being subjected to an external vibration, for example. The material of air-permeable envelope 29 is not limited to the resin and may be pulp-based or metal-based, as desired.

Dust bag 1 provided with deodorant 3a can be easily obtained by shaping air-permeable envelope 29 containing deodorant 3a therein in such a manner that it is fastened to inner envelope 28, when dust bag 1 is manufactured. In the ninth preferred embodiment, hydrophobic zeolite of 10 g is added into air-permeable envelope 29 as deodorant 3a, and then sealed.

Moreover, the surface of air-permeable envelope 29 made of resin may be coated with a silicon-based polymer to endow it with water-repellent properties. As a result, since deodorant 3a in air-permeable envelope 29 can retain its powder state and deodorizing performance for a long period of time, the deodorizing performance is not degraded even when the vacuum cleaner is not used for a while.

In envelope-shaped body 4, air-permeable envelope 29 may be fastened to the ceiling or front upper portion thereof so that deodorant 3a can be uniformly attached to dust and dirt in envelope-shaped body 4.

In the above configuration, deodorant 3a in air-permeable envelope 29 partially falls toward the dust and dirt via air-permeable ports due to an impact from the suction air flow generated when electric blower 16 is operated or due to a vibration resulting from a movement of main body 6. As a result, deodorant 3a is uniformly attached to the dust and dirt under the influence of the air flow. In such manner, the odor resulting from dust and dirt is adsorbed, and the odor included in the air discharged from the vacuum cleaner is reduced, thereby realizing pleasant cleaning environment.

Figure 14:
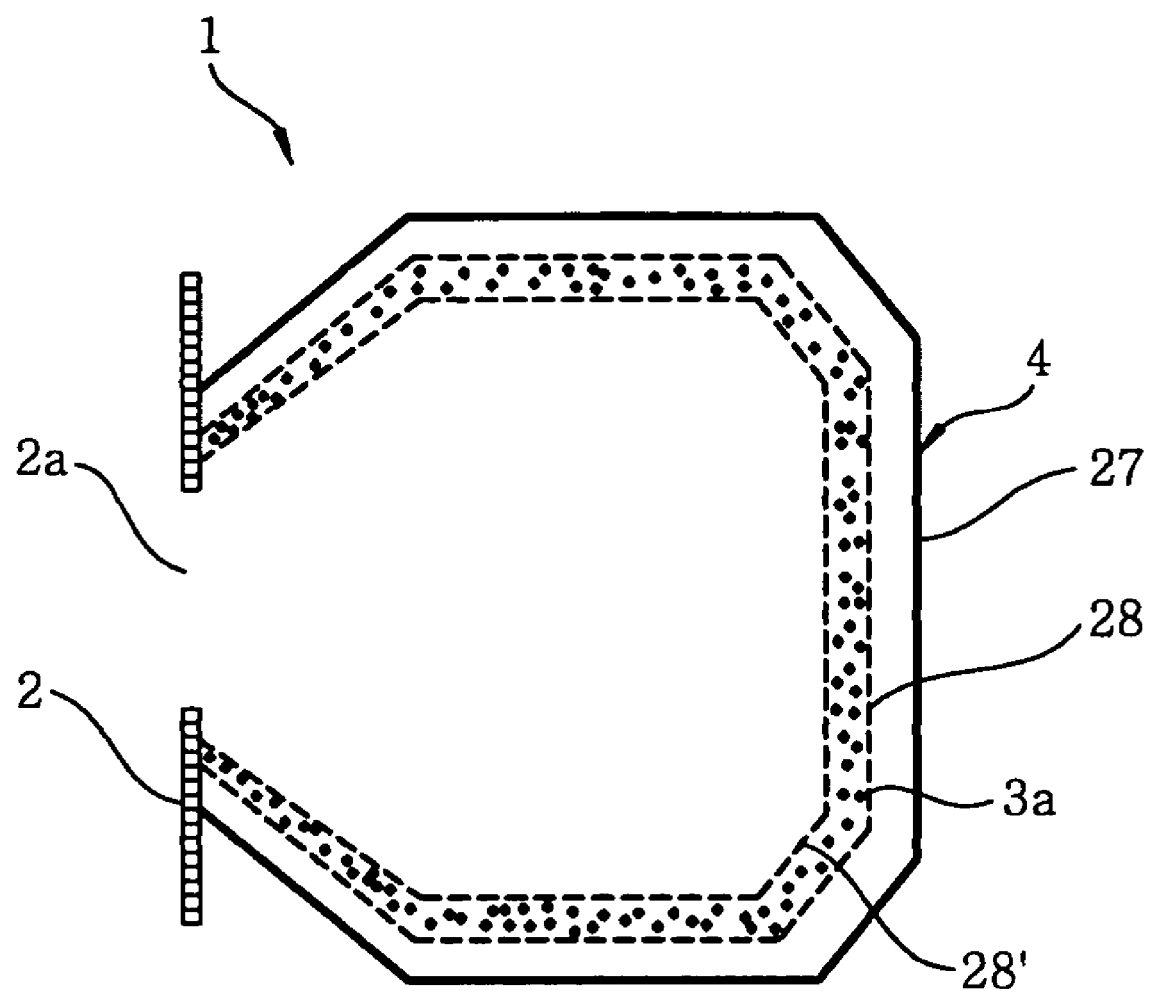
FIG. 14 is a cross sectional view briefly showing another dust bag for the vacuum cleaner in accordance with the ninth preferred embodiment of the present invention.

Further, as shown in FIG. 14, mesh envelope 28' may be provided inside inner envelope 28 of dust bag 1 and granular deodorant 3a may be loaded into a space between inner envelope 28 and mesh envelope 28'. An air-permeable diameter of mesh envelope 28' is set to be greater than a granule diameter of deodorant 3a, and air-permeable diameters of inner envelope 28 and outer envelope 27 are set to be smaller than the granule diameter of deodorant 3a. With such configuration, the same effect as the ninth preferred embodiment of the present invention can be obtained.

The vacuum cleaner and a dust bag for a vacuum cleaner in accordance with the present invention can substantially reduce the odor resulting from the dust and dirt included in the air discharged from the cleaner and maintain a deodorizing effect for a long period of time until the amount of the dust and dirt inside the dust bag reaches a threshold value.

While the invention has been shown and described with respect to the preferred embodiments, it will be understood by those skilled in the art that various changes and modifications may be made without departing from the scope of the invention as defined in the following claims.

What is claimed is:

1. A vacuum cleaner comprising:
   a dust chamber;
   a dust bag provided in the dust chamber; and
   an electric blower for generating suction air flow for drawing and collecting dust and dirt in the dust bag,
   wherein the dust bag includes:
   a core mounted inside the vacuum cleaner and provided with an opening for drawing in the dust and dirt;
   an envelop-shaped body for collecting the dust and dirt drawn via the opening of the core; and
   a storage case containing therein a deodorant of a granule or powder shape and fixed to a surface of the core, the surface being positioned downstream of the suction air flow, wherein the storage case is provided with an opening and a discharge port for communicating with the opening of the core, wherein a suction force by the suction air flow traveling through the opening of the core and the opening of the storage case to the envelope-shaped body acts on the inside of the storage case so that the deodorant is discharged from the discharge port and mixed with the dust and dirt before entering into the envelope-shaped body, such that a mixture of the deodorant and the dust and dirt spreads into the envelope-shaped body, and wherein one or more discharge ports for discharging the deodorant are provided on a surface of the storage case, the surface being substantially parallel to the air flow drawn via the opening of the core.

2. The vacuum cleaner of claim 1, wherein the deodorant is supplied into the dust bag at a weight ratio ranging from about 0.5 wt % to about 5 wt % with respect to the dust and dirt in the dust bag.

3. The vacuum cleaner of claim 1, wherein the deodorant has a granule diameter equal to or greater than 0.1 μm and equal to or less than 1 mm.

4. The vacuum cleaner of claim 1, wherein the deodorant includes at least one of hydrophobic zeolite, active carbon and transition metal oxide.

5. The vacuum cleaner of claim 1, wherein the deodorant has a functional material added thereto.

6. The vacuum cleaner of claim 5, wherein the functional material is a hygroscopic material.

7. The vacuum cleaner of claim 5, wherein the functional material serves to improve fluidity of the deodorant.

8. The vacuum cleaner of claim 5, wherein the functional material is an antibacterial material.

9. The vacuum cleaner of claim 5, wherein the functional material is an aromatic material.

10. A dust bag for a vacuum cleaner comprising:
a core mounted in the vacuum cleaner and provided with an opening for drawing in dust and dirt;
an envelope-shaped body for collecting the dust and dirt drawn via the opening of the core; and
a storage case containing therein a deodorant of a granule or powder shape and fixed to a surface of the core, the surface being positioned downstream of a suction air flow,
wherein the storage case is provided with an opening and a discharge port for communicating with the opening of the core,
wherein a suction force by the suction air flow traveling through the opening of the core and the opening of the storage case to the envelope-shaped body acts on the inside of the storage case so that the deodorant is discharged from the discharge port and mixed with the dust and dirt before entering into the envelope-shaped body, such that a mixture of the deodorant and the dust and dirt spreads into the envelope-shaped body, and
wherein one or more discharge ports for discharging the deodorant are provided on a surface of the storage case, the surface being substantially parallel to an air flow drawn via the opening of the core.

11. The dust bag for the vacuum cleaner of claim 10, wherein the dust bag is made of one or more flammable materials.

12. The dust bag for the vacuum cleaner of claim 10, wherein the deodorant is supplied into the dust bag at a weight ratio ranging from about 0.5 wt % to about 5 wt % with respect to the dust and dirt in the dust bag.

13. The dust bag for the vacuum cleaner of claim 10, wherein the deodorant has a granule diameter equal to or greater than 0.1 μm and equal to or less than 1 mm.

14. The dust bag for the vacuum cleaner of claim 10, wherein the deodorant includes at least one of hydrophobic zeolite, active carbon and transition metal oxide.

15. The dust bag for the vacuum cleaner of claim 10, wherein the deodorant has a functional material added thereto.

16. The dust bag for the vacuum cleaner of claim 15, wherein the functional material is a hygroscopic material.

17. The dust bag for the vacuum cleaner of claim 15, wherein the functional material serves to improve fluidity of the deodorant.

18. The dust bag for the vacuum cleaner of claim 15, wherein the functional material is an antibacterial material.

19. The dust bag for the vacuum cleaner of claim 15, wherein the functional material is an aromatic material.

20. A dust bag for a vacuum cleaner comprising:
a core mounted in the vacuum cleaner and provided with an opening for drawing in dust and dirt;
an envelope-shaped body for collecting the dust and dirt drawn via the opening of the core; and
a storage case containing therein a deodorant of a granule or powder shape and fixed to a surface of the core, the surface being positioned downstream of a suction air flow,
wherein the storage case is provided with an opening and a discharge port for communicating with the opening of the core,
wherein a suction force by the suction air flow traveling through the opening of the core and the opening of the storage case to the envelope-shaped body acts on the inside of the storage case so that the deodorant is discharged from the discharge port and mixed with the dust and dirt before entering into the envelope-shaped body, such that a mixture of the deodorant and the dust and dirt spreads into the envelope-shaped body, and
wherein the storage case is provided with a detachable cover member which serves to cover the discharge ports.

21. The dust bag for the vacuum cleaner of claim 20, wherein the deodorant is supplied into the dust bag at a weight ratio ranging from about 0.5 wt % to about 5 wt % with respect to the dust and dirt in the dust bag.

22. The dust bag for the vacuum cleaner of claim 20, wherein the deodorant has a granule diameter equal to or greater than 0.1 μm and equal to or less than 1 mm.

23. The dust bag for the vacuum cleaner of claim 20, wherein the deodorant includes at least one of hydrophobic zeolite, active carbon and transition metal oxide.

24. The dust bag for the vacuum cleaner of claim 20, wherein the deodorant has a functional material added thereto.

25. The dust bag for the vacuum cleaner of claim 24, wherein the functional material is a hygroscopic material.

26. The dust bag for the vacuum cleaner of claim 25, wherein the functional material serves to improve fluidity of the deodorant.

27. The dust bag for the vacuum cleaner of claim 25, wherein the functional material is an antibacterial material.

28. The dust bag for the vacuum cleaner of claim 25, wherein the functional material is an aromatic material.

* * * * *